(12) United States Patent
Zünd

(10) Patent No.: US 8,931,902 B2
(45) Date of Patent: Jan. 13, 2015

(54) ILLUMINATION DEVICE FOR A STEREOMICROSCOPE, IN PARTICULAR A SURGICAL MICROSCOPE

(71) Applicant: Leica Microsystems (Schweiz) AG, Heerbrugg (CH)

(72) Inventor: René Zünd, Widnau (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 119 days.

(21) Appl. No.: 13/663,797

(22) Filed: Oct. 30, 2012

(65) Prior Publication Data
US 2013/0107215 A1    May 2, 2013

(30) Foreign Application Priority Data
Oct. 31, 2011    (DE) .......................... 10 2011 085 527

(51) Int. Cl.
*A61B 3/10* (2006.01)
*A61B 3/13* (2006.01)
*G02B 21/06* (2006.01)
*G02B 21/22* (2006.01)

(52) U.S. Cl.
CPC ................ *A61B 3/132* (2013.01); *G02B 21/06* (2013.01); *G02B 21/22* (2013.01)
USPC .......................................... 351/214; 351/205

(58) Field of Classification Search
CPC .... G02B 21/22; G02B 21/0012; G02B 13/22; G02B 21/025; G02B 21/06; G02B 21/365; G02B 21/367; G02B 26/08; G02B 27/0075
USPC ................ 351/212, 214, 206, 204, 219, 221; 359/374, 376, 380
See application file for complete search history.

(56) References Cited

U.S. PATENT DOCUMENTS

| | | | |
|---|---|---|---|
| 6,011,647 A | 1/2000 | Geschwentner | |
| 2003/0043356 A1* | 3/2003 | Shiraishi | ........................ 355/53 |
| 2008/0297892 A1 | 12/2008 | Abele et al. | |
| 2009/0002812 A1 | 1/2009 | Kuster | |
| 2009/0273757 A1 | 11/2009 | Merz et al. | |
| 2012/0176769 A1 | 7/2012 | Reimer et al. | |

* cited by examiner

*Primary Examiner* — Thomas K Pham
*Assistant Examiner* — Sharrief Broome
(74) *Attorney, Agent, or Firm* — Hodgson Ross LLP

(57) ABSTRACT

The present invention relates to an illumination device for a stereomicroscope, in particular a surgical microscope for eye surgery, having at least one light source (10), a collector lens system (14), an aperture diaphragm (16), a condenser lens system (18), and an objective (22), illumination light being directed from the light source (10) through the collector lens system (14), the aperture diaphragm (16), the condenser lens system (18), and the objective (22) into the object plane (E19), the aperture diaphragm (16) being provided as a double orifice plate or four-orifice plate.

9 Claims, 3 Drawing Sheets

ILLUMINATION DEVICE FOR A STEREOMICROSCOPE, IN PARTICULAR A SURGICAL MICROSCOPE

CROSS REFERENCE TO RELATED APPLICATIONS

This application claims priority of German patent application number 10 2011 085 527.0 filed Oct. 31, 2011, the entire disclosure of which is incorporated by reference herein.

FIELD OF THE INVENTION

The present invention relates to an illumination device for a stereomicroscope, in particular a surgical microscope for eye surgery. The invention further relates to a stereomicroscope, in particular a surgical microscope, provided with an illumination device of this kind

BACKGROUND OF THE INVENTION

When stereomicroscopes are used as surgical microscopes in eye surgery, for certain applications the angle between the illumination axis and observation axis of the microscope must be minimized. The result of this is that the light rays incident perpendicularly onto the eye are reflected diffusely by the retina, and the lens capsule of the eye is therefore seen by reddish transmitted light. This effect is also known as the "red reflex." The quality of this red reflex is of critical importance, for example, in cataract extraction. In this procedure, after removal of the lens of the eye all the tissue residues must be removed from the eye. This can be achieved only if these tissue residues are presented with sufficient optical contrast.

EP 0 661 020 B1 discloses a switchable illumination device for a surgical microscope for eye surgery. The construction of this illumination system corresponds to a Köhler illumination system, such that in a first switch position the luminous-field diaphragm is imaged into the object plane, and the filament of the light source is imaged onto the retina of the eye. In at least one further switch position, the image of the filament can be shifted into the image plane of the field diaphragm. In order to ensure stereoscopic illumination, the illumination beam path is physically split using a beam splitter, in order to guide the light into the vicinity of the optical axes of the observation beam paths.

In complicated cases—for example caused by strong pigmentation of the patient's eye, a small pupil, or a high-grade cataract—the red reflex that is desirable in a cataract operation may not be as pronounced as a surgeon wishes. In such cases the red reflex can be so weakly pronounced that the eye to be operated on must be specially oriented in order to allow detection and removal of residues of the lens, which is destroyed during the operation.

The object that presents itself is therefore that of providing an illumination device for a surgical microscope in such a way that a red reflex can be efficiently made available even under the aforementioned difficult surgical conditions.

SUMMARY OF THE INVENTION

This object is achieved by an illumination device having an aperture diaphragm embodied as a double orifice plate having two orifices or a four-orifice plate having four orifices, and by a corresponding stereomicroscope having such an illumination device.

A significant increase in efficiency can be realized with the illumination device according to the present invention as compared with conventional red reflex illumination systems, and the total quantity of light acting on an eye undergoing surgery is reduced, making possible longer-duration operations without damaging the eye. According to the present invention, substantially all the light that strikes the eye undergoing surgery is used to generate the red reflex.

For example, it is possible to omit a diffusion filter that is conventionally used, which, by eliminating luminance maxima, enables unsharp imaging onto the retina of the light source being used, since the optics used according to the present invention does not cause sharp imaging of the filament onto the retina.

Advantageous embodiments are described herein.

Each orifice of the aperture diaphragm preferably has an (identical) diameter and an identical spacing from the optical axis of the illumination device.

It is particularly advantageous that the spacing of each orifice of the aperture diaphragm from the optical axis is provided adjustably. As a result, the stereo base of the illumination beam paths is adjustable, and can be adapted optimally to the observation beam paths and to the stereo base of the observation beam paths of the microscope.

It is furthermore advantageous to provide the diameter of the orifices of the aperture diaphragm variably or adjustably. The quantity of light striking the eye being observed can thereby be optimally adjusted.

According to a particularly preferred embodiment of the illumination device according to the present invention, the latter comprises a spherically concave mirror interacting with the light source. Thanks to the use of a spherical concave mirror of this kind, the illumination intensity of the light source can be effectively doubled with no need for a second light source. The fact that a second light source can be omitted makes possible a particularly compact design.

It proves to be particularly favorable in this context to arrange the light source in a manner decentered by a specific amount with respect to the optical axis of the illumination beam path. As a result of reflection at the spherical concave mirror, this then produces an image of the light source in the plane of the light source, which image is decentered with respect to the optical axis by the same amount in the opposite direction.

A beam splitter is expediently arranged between the condenser lens system and the objective. This beam splitter is preferably embodied as a physical beam splitter. By means of a beam splitter of this kind, the illumination beam paths and observation beam paths can be substantially superimposed onto one another.

The use of a beam splitter of this kind makes possible, in particular, a zero-degree illumination with reference to the observation beam paths.

It proves to be useful to additionally provide, in addition to a zero-degree illumination of this kind (for optimum observation of the red reflex), an ambient illumination, in particular a 6-degree illumination. Expediently, the illumination device can be switched back and forth between zero-degree and 6-degree illumination, simultaneous zero- and 6-degree illumination of course also being possible.

According to a particularly preferred embodiment of the illumination device according to the present invention, a luminous-field diaphragm is provided between the collector lens system and the aperture diaphragm. The illuminated field in the object plane can be sharply delimited by means of such a luminous-field diaphragm, with the result that undesired white reflexes, which are caused by the sclera of the patient's eye and are bothersome for the surgeon, can be avoided. The luminous-field diaphragm is arranged in the focal plane of the condenser lens system.

It is understood that the features recited above and those yet to be explained below are usable not only in the respective combination indicated, but also in other combinations or in isolation, without departing from the scope of the present invention.

The invention will now be described in further detail on the basis of a preferred exemplifying embodiment, with reference to the attached drawings.

DETAILED DESCRIPTION OF THE INVENTION

Figure 1:
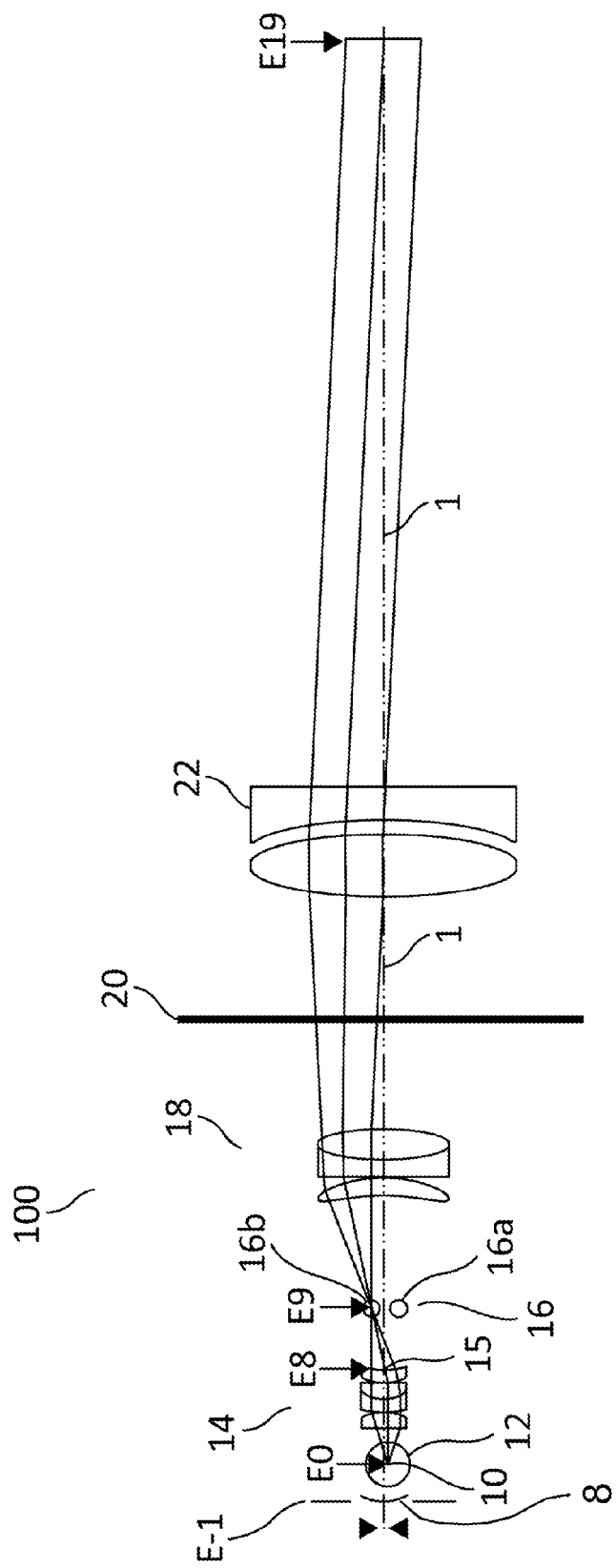
FIG. 1 is a simplified sectional view of a preferred embodiment of an illumination device according to the present invention with associated beam paths.

FIG. 1 depicts an illumination beam path in accordance with a preferred embodiment of the illumination device according to the present invention for a stereomicroscope, in "unfolded" form. In other words, in reality beam splitter 20 is introduced into the beam path at a 45° angle, as will be explained in further detail later on. For example, illumination light is typically initially introduced substantially horizontally (components to the left of deflection element 20 in FIG. 1) to the left of deflection element 20, and substantially vertically after deflection (components to the right of deflection element 20).

The preferred embodiment of the illumination device which is depicted is generally designated 100. Be it noted that only those components essential to an explanation of the invention are depicted. The depiction of deflection prisms, which can be used in addition to beam splitter 20 in order to effect a deflection of the beam path, has been omitted from the depiction in FIG. 1 for reasons of clarity.

A halogen filament, constituting light source 10, is arranged inside a glass cylinder 12 in a plane E0. As is evident from FIG. 1, halogen filament 10 is arranged with reference to optical axis 1 in a manner decentered by an amount x (downward with reference to optical axis 1 as depicted in FIG. 1).

A spherical concave mirror 8 is provided in a plane E-1 (to the left of plane E0 as depicted in FIG. 1). By reflection at this spherical concave mirror 8, halogen filament 10 is imaged back into plane E0 but with an opposite decentering with respect to the optical axis (an amount x above the optical axis).

The halogen filament provided in plane E0 is thus imaged directly, and on the other hand indirectly via spherical concave mirror 8, through a collector lens system 14 into a plane E9. For the sake of clarity, only the direct image of the halogen filament with its optical beam path is depicted in FIG. 1. The indirect image extends mirror-symmetrically with respect to optical axis 1. Hereby, the illumination intensity can be effectively doubled with no need to provide a further halogen filament.

Figure 2:
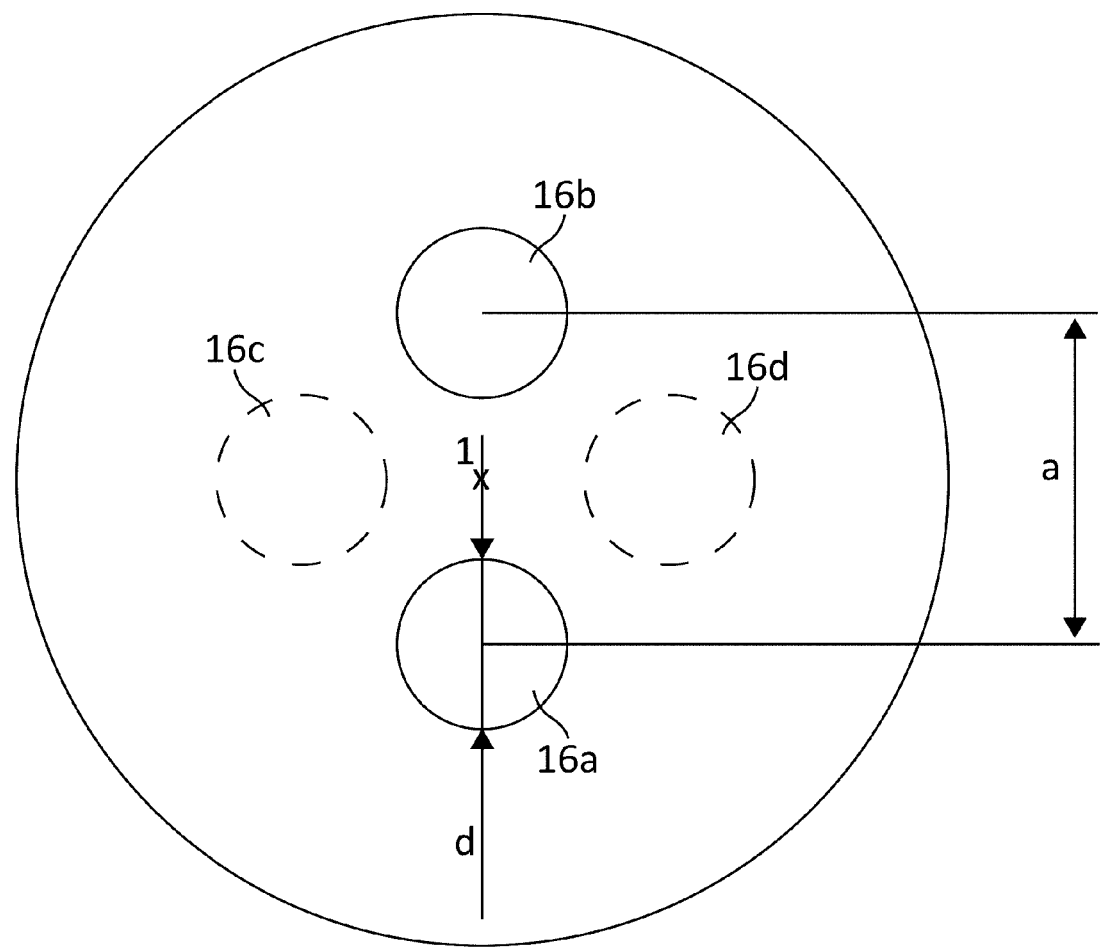
FIG. 2 is a schematic plan view of an aperture diaphragm usable according to the present invention.

A double orifice plate 16 is arranged in plane E9 as an aperture diaphragm. This aperture diaphragm 16 is depicted in FIG. 2, and comprises at least two orifices 16a, 16b that each have a diameter d and have a spacing a/2 from the optical axis. The spacing of the center points of orifices 16a, 16b is thus equal to a.

Orifices 16a, 16b are depicted in FIG. 1 entirely schematically (rotated 90° for elucidation purposes).

Collector lens system 14 images halogen filament 10 into plane E9 at the location of orifice 16a of aperture diaphragm 16. Analogously, the image of halogen filament 10 in plane E0 generated by means of spherical concave mirror 8 is imaged onto second orifice 16b of aperture diaphragm 16.

Aperture diaphragm 16, embodied as a double orifice plate or stop, thus serves firstly for mechanical (or geometric) separation of two illumination beam paths that are embodied as stereoscopic beam paths, as will be further explained below. Physical separation of the illumination beam paths, as known from the existing art, can thus be dispensed with. The result is that absorption losses, which conventionally occur when a physical beam splitter is used, can be avoided.

Aperture diaphragm 16 also serves to eliminate undesired sources of stray light.

After passing through aperture diaphragm 16, the beam paths encounter a condenser lens system 18 that virtually images plane E9 into the focal plane of objective 22. A collimated light beam or illumination beam path thus exists between objective 22 and the patient's eye located in plane E19. In other words, the overall result is that light source 10 is imaged at infinity, and is imaged, by means of the eye lens arranged in a plane E19 (object plane), onto the retina of the patient's eye being observed or operated on. This beam profile generates sharply defined spots of light on the retina of the patient's eye; this is necessary and desirable for generating high contrast within the capsule (envelope of the eye lens).

Coaxial illumination is necessary in order to provide the best possible red reflex, i.e. optical axis 1 of the illumination beam path should be superimposed to the greatest extent possible onto the optical axis of the observation beam path. Small deviations, for example of up to 2°, in particular from 0.5° to 1.5°, are negligible in this context, and produce little or no decrease in the quality of the red reflex. This requirement is met by means of beam splitter 20 already mentioned, whose split ratio (ratio of reflection to transmission) can be, for example, 20:80. In terms of selection of the proportion of reflection and transmission, a tradeoff exists between the delivery of sufficient light intensity to the patient's eye and the greatest possible light intensity delivered from the patient's eye, through the microscope to the observer's (surgeon's) eye. The greater the reflection proportion of beam splitter 20, the more light travels from light source 10 to the patient's eye, while at the same time the less light travels from the patient's eye through the microscope to the surgeon.

Particular properties and possible variations of aperture diaphragm 16 will be discussed below, once again with reference to FIG. 2.

When only the two previously discussed orifices 16a, 16b are provided, aperture diaphragm 16 represents a double orifice plate. The provision of further orifices 16c, 16d (shown with dashed lines in FIG. 2) makes available a four-orifice plate or a "double-double orifice plate". By means of this kind of configuration, an excellent red reflex can also be generated for a second observer (assistant to the surgeon), by the fact that the additional illumination beam paths which can thereby be made available are superimposed onto the observation beam paths for the assistant.

Modifying the diameter d of the orifices of aperture diaphragm 16 also allows the diameter of the respective spots of light on the retina of the patient's eye to be modified. At the same time, the quantity of light delivered onto the patient's eye can thereby also be varied. The orifices of aperture diaphragm 16 are therefore usefully provided with a variable diameter, so that a surgeon and/or an assistant can perform, before or during the operation, an optimum adaptation of the aperture diaphragm to the specific circumstances.

In addition, the spacing a between the two orifices 16a, 16b, and the corresponding spacing between orifices 16c, 16d, can be provided variably. Varying these spacings allows the stereo base of the two illumination beam paths to be adjusted, and to be adapted as accurately as possible to the stereo base of the corresponding observation beam paths.

It proves to be particularly advantageous to provide a further diaphragm in a plane E8 between collector lens system 14 and aperture diaphragm 16. This is a luminous-field diaphragm 15. Provision of a luminous-field diaphragm of this kind in plane E8 results in the implementation of a Köhler illumination. Luminous-field diaphragm 15 (and thus plane E8) is located in the focal plane of condenser lens system 18, with the result that an image of the field diaphragm at infinity is generated. Provision of the luminous-field diaphragm 15 ensures that objective 22 generates a sharply delimited illuminated or luminous-field in plane E19. As a result the luminous-field can, for example, be selected so that white reflexes caused by the sclera, which are bothersome to the surgeon, can be avoided.

FIG. 3 once again shows the preferred imaging of field diaphragm 15 into the luminous field in plane E19 (cornea of the patient's eye). The light beam proceeding from field diaphragm 15 in plane E8 can be seen. As already mentioned, field diaphragm 15 is located in the focal plane of condenser lens system 18. After passage through condenser lens system 18, objective 22 produces sharp imaging into plane E19. The overall result is the sharply delimited luminous field, already mentioned, in plane E19.

Figure 3:
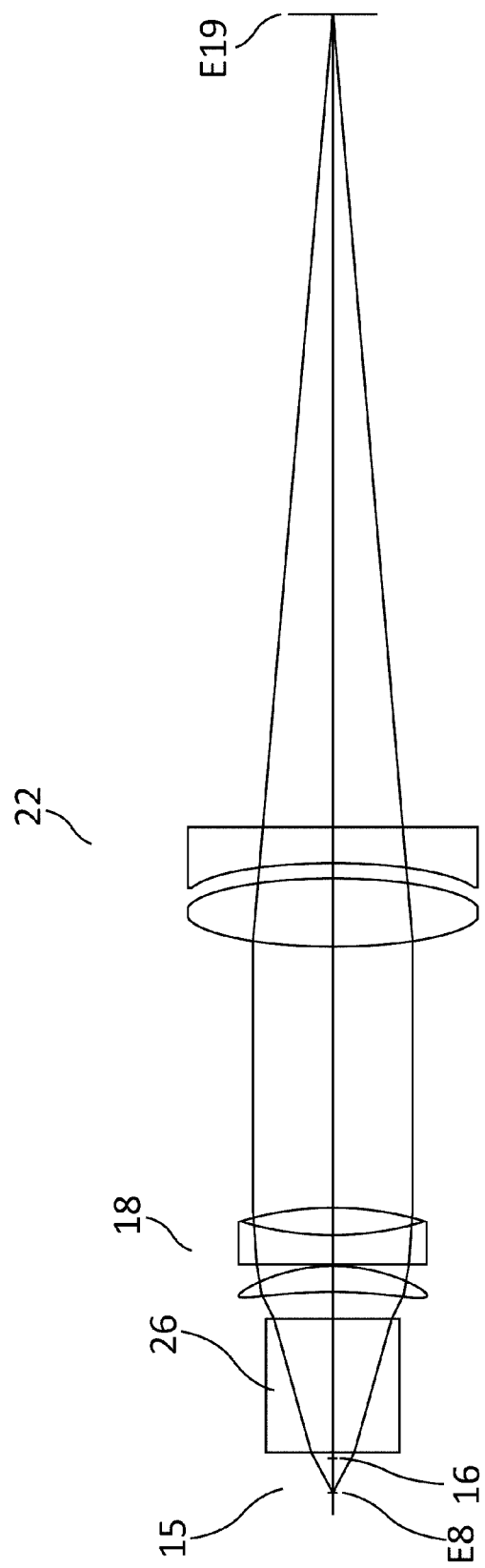
FIG. 3 is a sectional view, corresponding to FIG. 1, with which the preferred imaging of the luminous-field diaphragm into the luminous-field is illustrated.

According to a preferred embodiment as depicted in FIGS. 1 and 3, condenser lens system 18 is made up of three lenses, and objective 22 of two lenses. Embodiments having different numbers of lenses are of course possible and usable.

In the depiction of FIG. 3, a prism or prism system 26, with which the illumination beam path can be deflected and/or constricted before encountering beam splitter 20 shown in FIG. 1, is depicted between the likewise shown aperture diaphragm 16 and condenser lens system 18. The use of this kind of prism or prism system 26 is optional. Advantageously, it serves for precise guidance of the illumination beam path. Prism or prism system 26 is depicted in unfolded fashion, analogously to the depiction of beam splitter 20 in FIG. 1. Beam splitter 20 is not shown in FIG. 3.

As already mentioned above, the halogen filament is firstly imaged into plane E9 of aperture diaphragm 16. This imaging occurs in such a way that the luminance differences (between luminance maxima and luminance minima) identifiable in the halogen filament are reduced. In particular, the light intensity of the luminance maxima is reduced. Because plane E9 is conjugated with the retina of the patient's eye, and because the luminance maxima on the retina are thus also reduced, it would be possible to omit a diffusion filter that is utilized in conventional illumination devices. It is preferred, however, to use such a diffusion filter, which can be arranged e.g. in the collector lens system. The efficiency of the illumination beam path is thereby significantly increased.

Advantageously, baffle plates or scattered light screens are provided between light source 10 and beam splitter 20 (not depicted in FIG. 1). This makes it possible to prevent the observation beam paths from being negatively influenced by the illumination beam paths superimposed onto them.

It is useful to provide, in addition to the red reflex illumination shown, an ambient illumination that can likewise be embodied as a Köhler illumination. The optical axis of this beam path, which is separated from the red reflex illumination, typically forms an angle of approximately 6° with the optical axis of the observation beam path. It is therefore also called "6-degree illumination."

PARTS LIST

E-1, E0, E8, E9, E19 Planes on optical axis
1 Optical axis
10 Light source (halogen filament)
12 Glass cylinder
14 Collector lens system
16 Aperture diaphragm
16a, 16b, 16c, 16d Orifices in aperture diaphragm
18 Condenser lens system
20 Beam splitter
22 Objective
26 Prism (prism system)
100 Illumination device
a Spacing of orifices of aperture diaphragm
d Diameter of orifices of aperture diaphragm

What is claimed is:

1. An illumination device for a stereomicroscope for eye surgery, the illumination device comprising: an optical axis; at least one light source decentered by a non-zero amount (x) with respect to the optical axis a spherically concave mirror interacting with the light source to form an indirect image of the light source oppositely decentered from the light source by a non-zero amount with respect to the optical axis; a collector lens system; an aperture diaphragm; a condenser lens system; and an objective; wherein illumination light is directed from the light source through the collector lens system, the aperture diaphragm, the condenser lens system, and the objective into an object plane of the stereomicroscope, and wherein the aperture diaphragm is a double orifice plate having two orifices or a four-orifice plate having four orifices.

2. The illumination device according to claim 1, wherein each orifice of the aperture diaphragm has a diameter and a spacing (a/2) from the optical axis of the illumination device.

3. The illumination device according to claim 2, wherein the spacing (a/2) of each orifice of the aperture diaphragm from the optical axis is adjustable.

4. The illumination device according to claim 2, wherein the diameter of the orifices of the aperture diaphragm is adjustable.

5. The illumination device according to claim 1, further comprising a beam splitter arranged between the condenser lens system and the objective.

6. The illumination device according to claim 1, wherein the illumination device provides a zero-degree illumination with reference to observation beam paths of the stereomicroscope.

7. The illumination device according to claim 6, further comprising an ambient illumination system providing a six-degree illumination with reference to the observation beam paths of the stereomicroscope.

8. The illumination device according to claim 1, further comprising a luminous-field diaphragm between the collector lens system and the aperture diaphragm.

9. A stereomicroscope for eye surgery comprising an illumination device according to claim 1.

* * * * *